(12) United States Patent
McDermott

(10) Patent No.: US 7,764,379 B1
(45) Date of Patent: Jul. 27, 2010

(54) SEMICONDUCTOR LASER NATURAL GAS ANALYSIS SYSTEM AND METHOD

(75) Inventor: Lawrence McDermott, Groton, MA (US)

(73) Assignee: Axsun Technologies, Inc., Billerica, MA (US)

(*) Notice: Subject to any disclaimer, the term of this patent is extended or adjusted under 35 U.S.C. 154(b) by 0 days.

(21) Appl. No.: 11/613,291

(22) Filed: Dec. 20, 2006

Related U.S. Application Data

(60) Provisional application No. 60/752,303, filed on Dec. 20, 2005, provisional application No. 60/775,465, filed on Feb. 21, 2006.

(51) Int. Cl.
*G01N 21/00* (2006.01)
(52) U.S. Cl. .................................................. 356/437
(58) Field of Classification Search ................... 356/437
See application file for complete search history.

(56) References Cited

U.S. PATENT DOCUMENTS

| | | | |
|---|---|---|---|
| 2,286,985 A * | 6/1942 | Hanson ...................... | 356/437 |
| 5,822,058 A | 10/1998 | Adler-Golden et al. | |
| 6,038,023 A | 3/2000 | Carlson et al. | |
| 6,072,576 A | 6/2000 | McDonald et al. | |
| 6,157,455 A * | 12/2000 | Pinvidic et al. ............. | 356/437 |
| 6,420,695 B1 | 7/2002 | Grasdepot et al. | |
| 6,536,946 B1 | 3/2003 | Froelich et al. | |
| 6,539,775 B2 | 4/2003 | Driftmeier | |
| 6,552,793 B1 | 4/2003 | Kastner | |
| 6,555,820 B1 | 4/2003 | Tacke et al. | |
| 6,559,945 B1 | 5/2003 | Grasdepot | |
| 6,590,647 B2 | 7/2003 | Stephenson | |
| 6,941,230 B1 | 9/2005 | Stirnberg et al. | |
| 7,298,490 B2 * | 11/2007 | Baer et al. .................. | 356/454 |
| 2001/0054900 A1 | 12/2001 | Yokoyama et al. | |
| 2004/0120366 A1 * | 6/2004 | Chang et al. ................... | 372/20 |
| 2006/0044562 A1 * | 3/2006 | Hagene et al. .............. | 356/437 |

FOREIGN PATENT DOCUMENTS

| EP | 0 822 977 A1 | 12/1998 |
|---|---|---|
| EP | 1 070 955 A2 | 1/2001 |
| EP | 1 141 677 B1 | 7/2002 |

OTHER PUBLICATIONS

Brown, Chris W. et al., "Feasibility of On-line Monitoring of the BTU Content of Natural Gas with a Near-Infrared Fiber Optic System," Applied Spectroscopy, vol. 47, No. 6, pp. 812-815, 1993.

Goldstein, N. et al., "Real-Time Optical BTU Measurement of Natural Gas at Line Pressure," 4th International Symposium on Fluid Flow Measurement, Denver, Colorado, 13 pages, Jun. 27-30, 1999.

Somesfalean, G. et al., "Temporal correlation scheme for spectroscopic gas analysis using multimode diode lasers," Applied Physics Letters 86, 184102, 3 pages, 2005.

* cited by examiner

*Primary Examiner*—Tarifur Chowdhury
*Assistant Examiner*—Tara S Pajoohi
(74) *Attorney, Agent, or Firm*—Houston Eliseeva LLP

(57) ABSTRACT

A system of gas property monitoring comprises a gas cell for containing a gas of interest and a semiconductor tunable laser spectroscopy system for generating a tunable signal that is transmitted through the gas of interest in the gas cell and detecting the tunable signal after transmission through the gas of interest. An analyzer is provided for relating a spectral response of the gas of interest to a property of interest, such as an energy content of the gas of interest.

17 Claims, 4 Drawing Sheets

SEMICONDUCTOR LASER NATURAL GAS ANALYSIS SYSTEM AND METHOD

RELATED APPLICATIONS

This application claims the benefit under 35 USC 119(e) of Provisional Application Nos. 60/752,303, filed on Dec. 20, 2005 and 60/775,465, filed Feb. 21, 2006, both of which are incorporated herein by this reference in their entirety.

BACKGROUND OF THE INVENTION

BTU (British Thermal Unit) or energy-content monitors are used to analyze the BTU content of natural gas at producing wells and transfer points, and also at the points of consumption. Previous work has showed the possibility of accurately performing this analysis by near infrared (NIR) spectroscopy, but commercially available instrumentation was too complex and expensive to be deployed widely. Instead gas chromatographs (GC) are currently used widely to perform this BTU monitoring. Nonetheless, there are several advantages to using NIR for this analysis including lower total cost of ownership, lower maintenance, faster response (seconds instead of minutes or tens of minutes), and the NIR approach requires no consumables such as carrier and fuel gases required by the GC.

In a GC analysis, the hydrocarbons present in the natural gas are separated based on the retention time on a heated column. The BTU or energy content is calculated by summing up the concentration of the different hydrocarbon species and applying published mathematical equations.

NIR based analysis operates on a different principle. A spectrum of the sample is collected. Light at different wavelengths is absorbed based on the concentration of functional groups, such as C—H, C=C—H, C≡C—H, N—H, and O—H, present in the molecules of the gas. The spectrum of the natural gas is a sum of the different species present such as methane, ethane, isobutene, n-butane, propane, etc.

Mathematical models based on chemometrics derive a relationship between the spectra and the concentration of the property of interest, such as BTU or energy content. The resulting calibration model is applied to each spectrum from the gas, and the BTU content can be reported to a local control or data logging system.

SUMMARY OF THE INVENTION

In general according to one aspect, the invention features a system of gas property monitoring. It comprises a gas cell for containing a gas of interest and a semiconductor tunable laser spectroscopy system for generating a tunable signal that is transmitted through the gas of interest in the gas cell and detecting the tunable signal after transmission through the gas of interest. An analyzer is provided for relating a spectral response of the gas of interest to a property of interest, such as an energy content of the gas of interest.

In a preferred embodiment, a pressure sensor for determining a pressure of the gas of interest and a temperature sensor for determining a temperature of the gas of interest are further provided. The analyzer may use the pressure and the temperature to normalize the spectra before chemometric analysis is used to determine the property of interest. In a further modification, a hydrogen concentration sensor is provided. This sensor is used to detect the presence and amount of hydrogen in the gas of interest to address the situation where the narrow spectral signatures of the hydrogen are not able to be accurately detected by the broader spectral linewidth of the tunable laser.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

Figure 1:
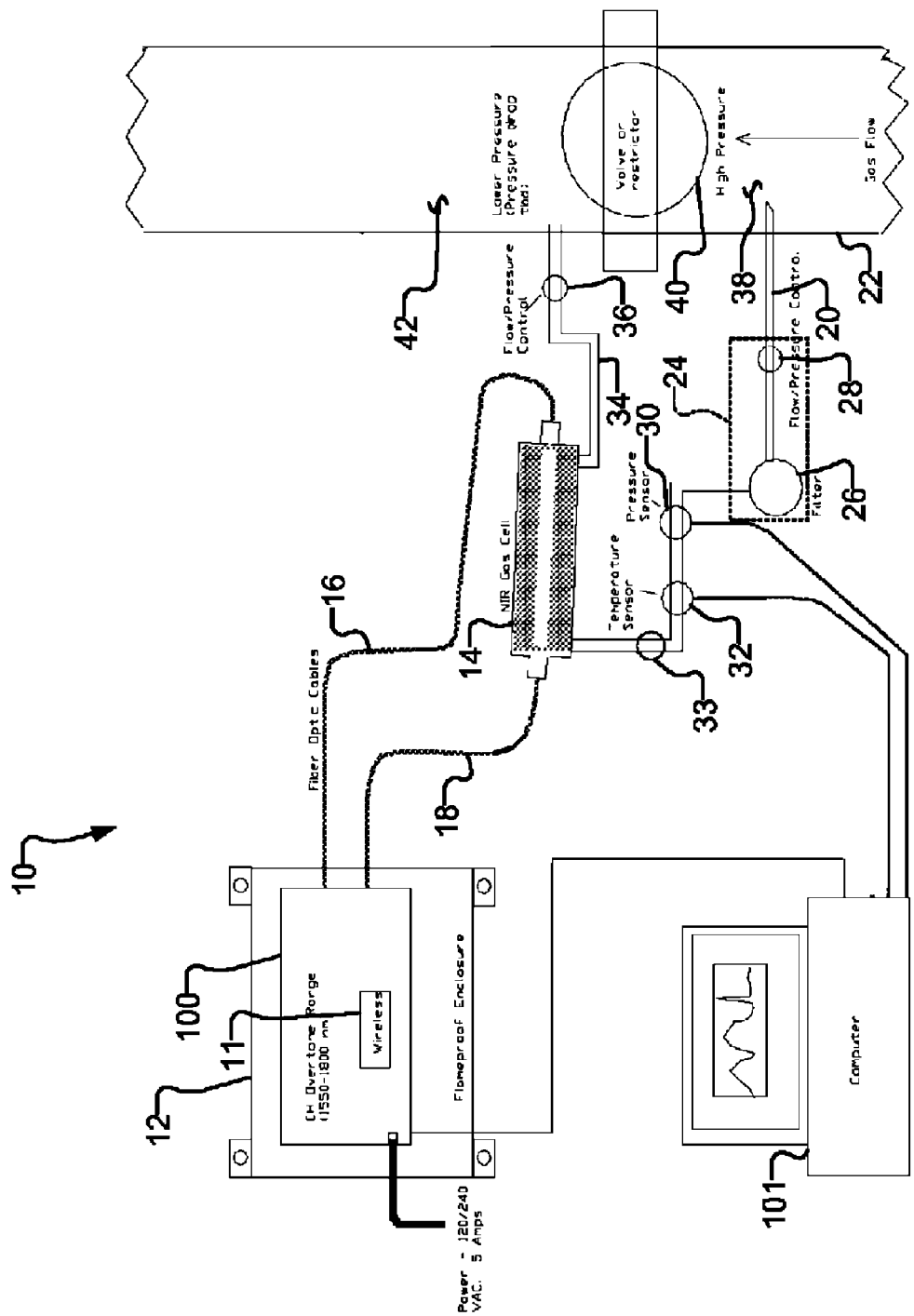
FIG. 1 is a schematic diagram showing a BTU or energy-content monitoring system according to an embodiment of the invention.

FIG. 1 shows a system configuration for a BTU or energy-content monitoring system 10, which has been constructed according to the principles of the present.

The system 10 comprises a spectroscopy system 100, enclosed in an explosion proof enclosure 12. In one implementation, the spectroscopy system 100 further comprises a wireless data interface 11, supporting an 802.11b communications interface for control of the spectroscopy system and for uploading of spectroscopic data from the system 100 to an analyzer computer 101.

The spectroscopy measurements are taken in a gas cell 14. In one example, the cell 14 is designed to operate in the wavelength range from 1550-1800 nanometers (nm) at ambient temperatures (0 to +50° C.) and pressures up to 600 pounds per square inch (psi). Under normal operating conditions, the cell 14 will be at ambient (<60° C.) temperature and 100 psi.

Two stainless steel-clad fiber optic cables 16, 18 connect the spectroscopy system 100 to the gas cell 14. The configuration is suitable for monitoring of natural gas. Specifically, a tunable laser signal from the spectroscopy system 100 is transmitted to the gas cell 14 in output cable 16. The tunable laser signal then propagates through the gas atmosphere in the gas cell 14. The laser signal is then collected into the input cable 18 for transmission to the spectroscopic system detector 100. In this example, the light output from the spectroscopy system 100 on the output fiber 16, which is single mode optical fiber with polarization control such as polarization maintaining or other polarization controlling fiber.

A sample probe/tap 20 is installed into the gas line 22. This extracts a representative sample of gas and transports it to a sample conditioning system 24. The sample conditioning system 24 removes water and any condensate present, using a filter 26. It also controls the pressure and flow to/through the gas cell using a first flow/pressure control valve 28 and a second flow/pressure control valve 36.

A pressure sensor 30 and a temperature sensor 32 are also installed in-line with the sample cell 14. The pressure and temperature sensors 30, 32 are read by the analyzer 101 and logged to enable compensation of the spectroscopy data based on a pressure and temperature.

In a further embodiment, a hydrogen concentration sensor 33 is provided in line with the pressure and temperature sensors 30, 32. This hydrogen sensor is used to detect the presence and amount of hydrogen gas, diatomic hydrogen, in the gas of interest to address the situation where the narrow spectral signatures of the hydrogen are not able to be accurately detected by the broader spectral linewidth of the tunable laser of the spectroscopy system 100.

The gas of interest continuously flows through the flow cell 14 and is scanned and analyzed. After exiting the gas cell, the gas can be returned to a low pressure point 42. Specifically, a valve or restrictor 40 is used to create a pressure gradient between a high pressure region 38, where the gas sample is drawn from, and the low pressure region 42 where the gas is returned to the pipe 22. In another embodiment, the sampled gas is flared.

The analyzer 101 contains mathematical models based on chemometrics that relate the spectral data from the spectroscopy system 100, the temperature data from temperature sensor 32, hydrogen concentration from the hydrogen detector 33, and pressure data from pressure 30 to the concentration of the property of interest, such as BTU or energy content. The resulting calibration model is applied to each spectrum generated by the spectroscopy system 100 from the gas in the gas cell 14, and the BTU concentration is reported to a local control or data logging system.

Figure 2:
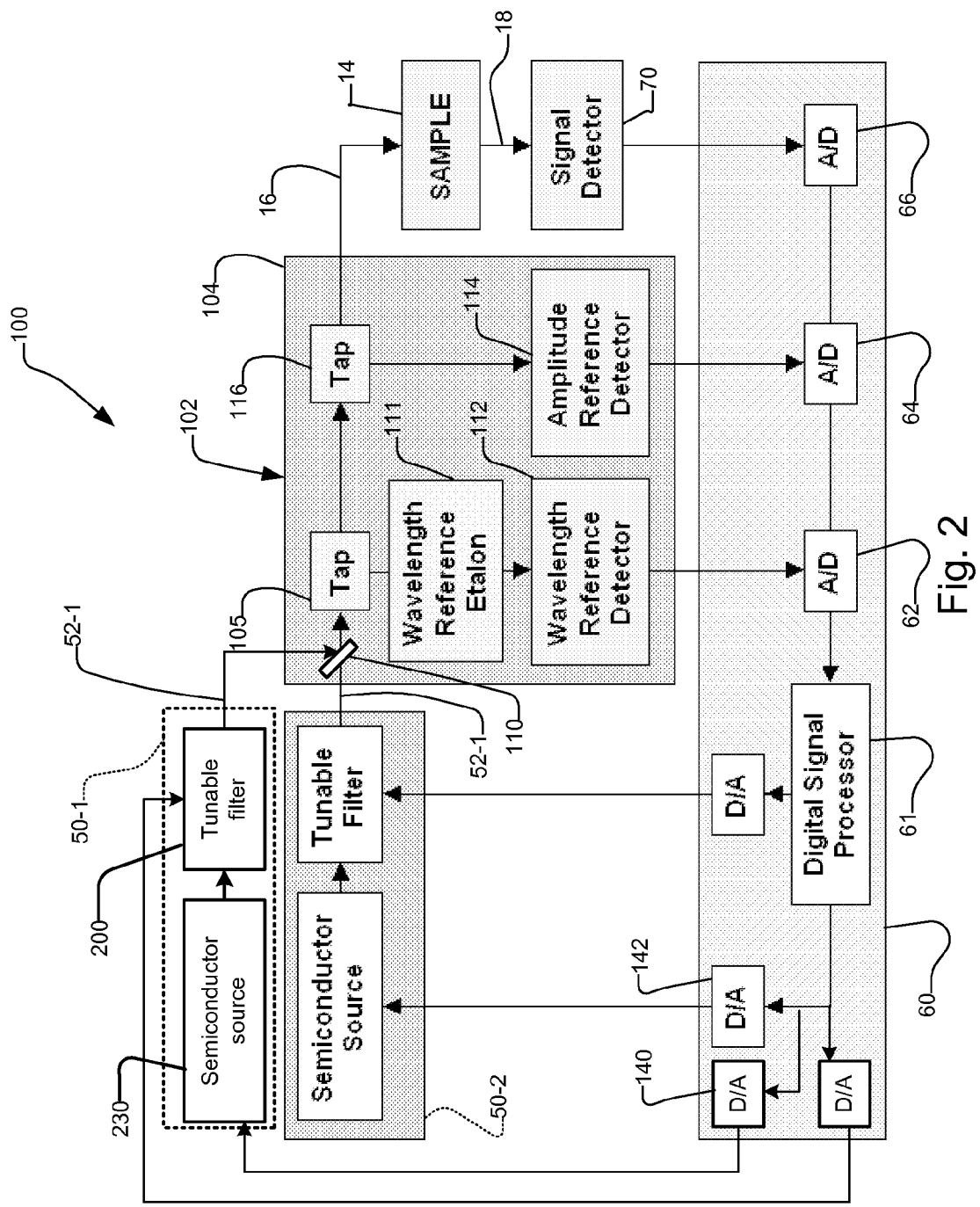
FIG. 2 is block diagram of the spectroscopy system of the monitoring system according to an embodiment of the invention.

FIG. 2 shows the spectroscopy system 100 according to one embodiment. This system is discussed in more detail in U.S. patent application Ser. No. 11/419,993, filed May 23, 2006, by Flanders, et al., which is incorporated herein by this reference in its entirety.

In one embodiment, two tunable semiconductor sources 50-1 and 50-2 are provided to generate tunable signals in different, adjacent spectral bands to increase spectral range. In a current embodiment, only a single source is used that emits in the range from 1550 to 1800 nm. The tunable sources 50-1, 50-2 have corresponding semiconductor chips 230 that are paired with microelectromechanical (MEMS) Fabry Perot tunable filters 200 to create external cavity tunable lasers (ECL).

Each of semiconductor sources 230 and tunable filters 200 of the tunable sources 50-1, 50-2 are controlled by a system controller 60. Specifically a digital signal processor core 61 drives the sources and tunable filters via separate digital to analog converters D/A 140, 142.

Respective single mode optical fibers 52-1 and 52-2 carry the tunable signals from each of the sources 50-1, 50-2.

A wavelength amplitude referencing system 102 combines the tunable signals from each of the sources 50-1, 50-2 onto the output fiber 16 while also performing amplitude and wavelength detection.

In more detail, a polarizing beam combiner 110 is used to combine the tunable signals for each of the sources. A wavelength reference tap 105 directs a portion of the combined beam to a quartz reference etalon 111 and a wavelength reference detector 112. An amplitude reference tap 116 directs a portion of the combined beam to an amplitude reference detector 114. Each of these detectors 112, 114 is monitored by the system controller 60 via separate analog to digital converters 62, 64.

In operation, the tunable filters 200 are continuously scanned over the spectral scan band. The tunable signal is transmitted to the gas sample of interest in gas cell 14 via the output optical fiber 16. The tunable signal from the sample is then collected on the input fiber and transmitted to a signal detector 70, connected to the input fiber 18, is then digitized by the detector's analog to digital converter 66. In one embodiment, the typical measurement time is less than 2 seconds (with signal averaging). The digital to analog converter 66 samples the detector 70 to provide a resolution of greater than 3.5 cm$^{-1}$.

In the preferred embodiment, every point of every scan is referenced. As the sources 50-1, 50-2 of the spectrometer scan, the signal from the wavelength reference detector 112 is a fringe pattern, analogous to the He-Ne reference signal in an FT-IR. This provides real-time wavelength referencing.

An optical bench 104 on which the reference system 102 is implemented is thermostat-controlled, ensuring both short- and long-term dimensional stability for the etalon 110, and thus both short- and long-term wavelength reproducibility.

Figure 3:
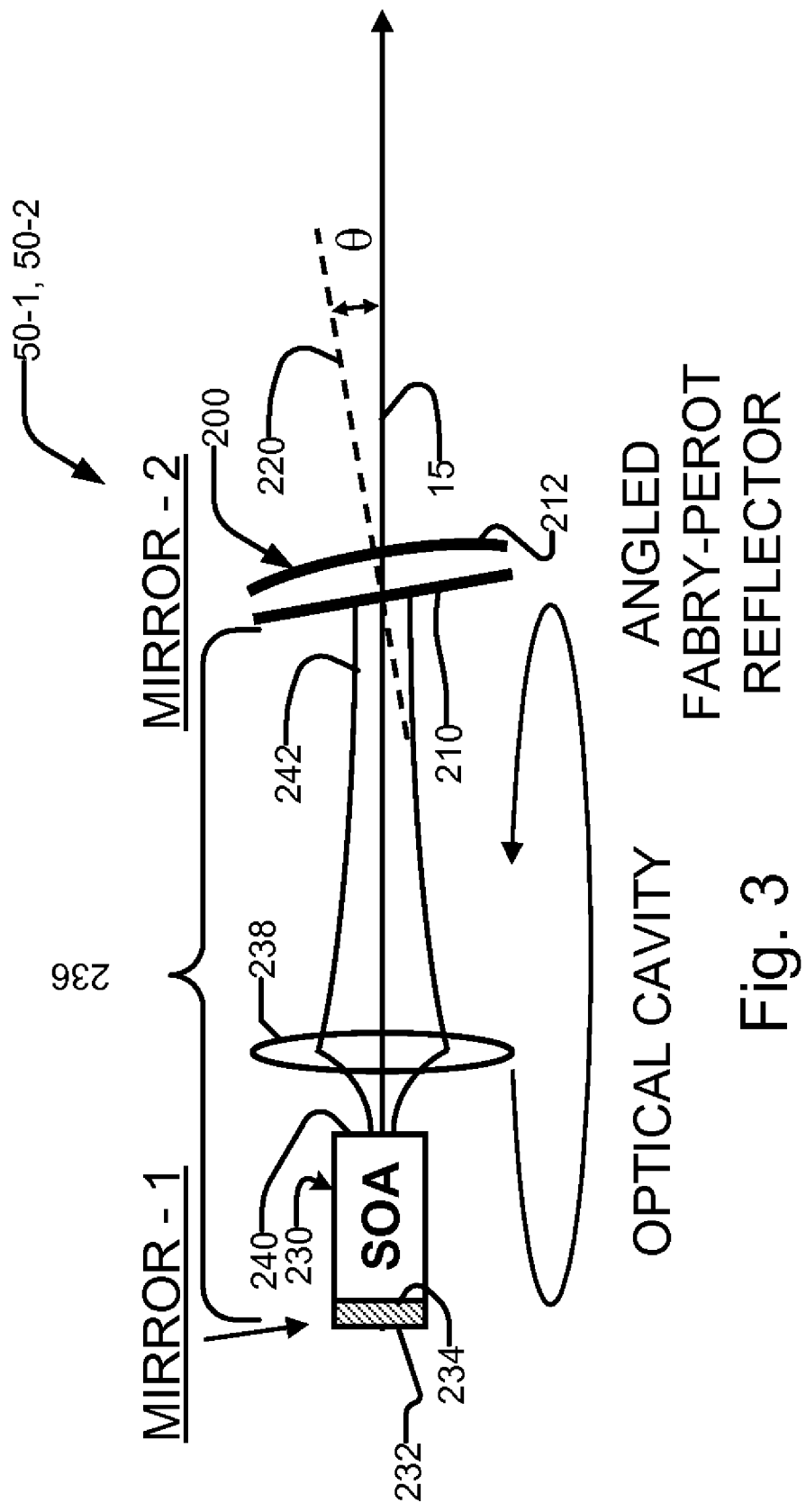
FIG. 3 illustrates an external cavity laser used in the spectroscopy system of one embodiment.

FIG. 3 illustrates an embodiment of the tunable ECL's in the tunable sources 50-1, 50-2. This ECL system is discussed in more detail in U.S. patent application Ser. No. 11/158,617, filed Jun. 22, 2005, by Flanders, et al., which is incorporated herein by this reference in its entirety.

In a current embodiment, a reflective SOA 230 is used. As a result, a first mirror of the laser cavity 236 is a facet 234 of the SOA gain chip 230 that has a highly reflecting (HR) coating 232. The other mirror of the laser cavity 236 is provided by an angled MEMS Fabry-Perot tunable filter 200 comprising an opposed curved mirror 212 and a flat mirror 210. An intracavity lens 238 is used to collimate or collect the light from an AR coated facet 240 of the SOA 230 and generally form a beam waist 242 to launch the light into the resonant filter 200 and then couple light from the filter 200 back into the chip 230.

In this example, the light output from the laser cavity 236 is provided to the output fiber 16, which is single mode fiber with polarization control such as polarization maintaining or other polarization controlling fiber.

Figure 4:
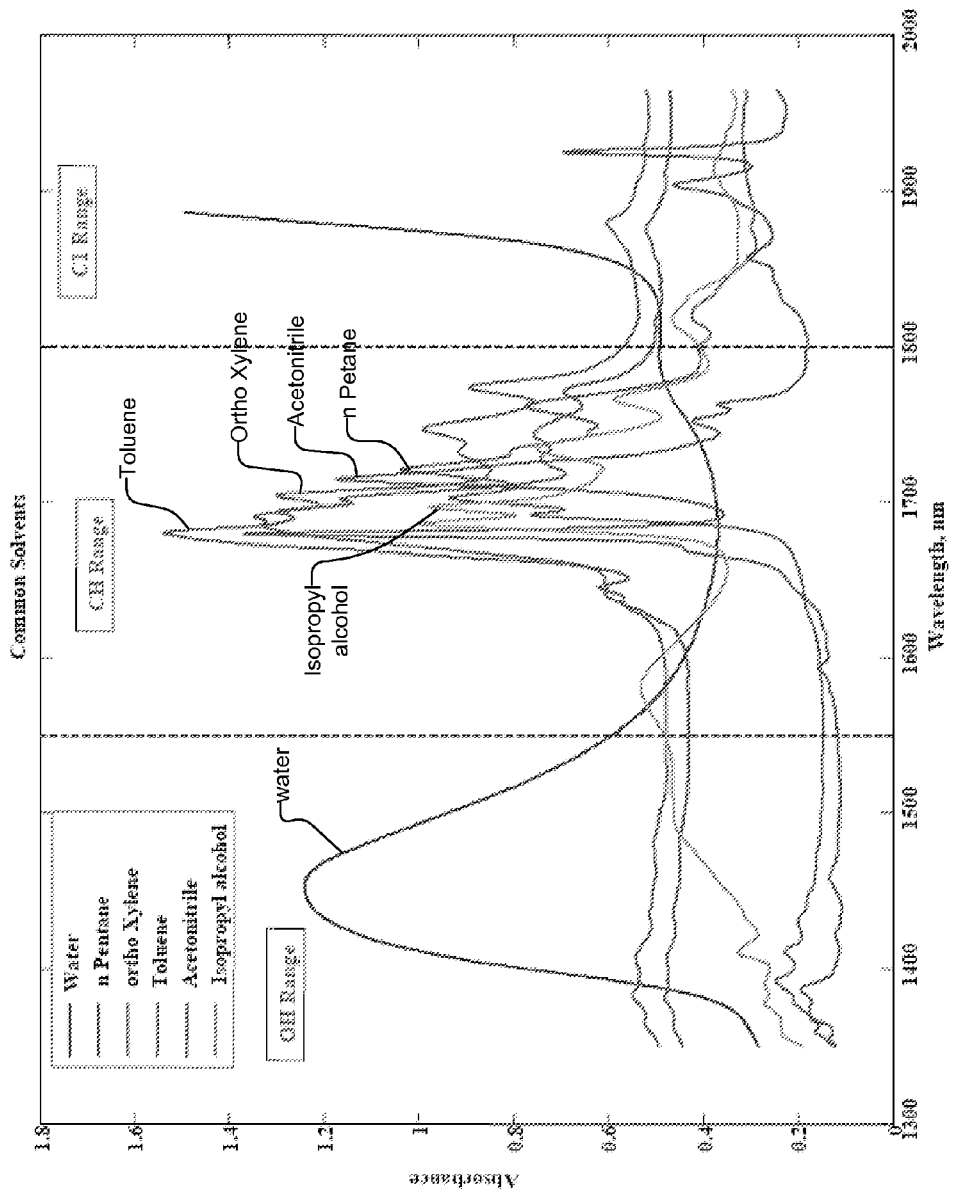
FIG. 4 is a plot showing the spectral response of exemplary natural gas components.

FIG. 4 shows the spectral responses of some representative components of natural gas and other hydrocarbons. As illustrated, the CH range, from 1550 to 1800 nm provides unique signatures for the components, while having relatively low water absorption.

While this invention has been particularly shown and described with references to preferred embodiments thereof, it will be understood by those skilled in the art that various changes in form and details may be made therein without departing from the scope of the invention encompassed by the appended claims.

What is claimed is:

1. A system of gas property monitoring, comprising:

a gas cell for containing a gas of interest;

a semiconductor tunable laser spectroscopy system for generating a tunable signal that is transmitted through the gas of interest in the gas cell and detecting the tunable signal after transmission through the gas of interest to determine a spectral response of the gas of interest, wherein a spectral width of the tunable signal from the semiconductor tunable laser spectroscopy system is too broad to accurately detect a concentration of diatomic hydrogen due to associated narrow spectral lines of the diatomic hydrogen;

a hydrogen sensor for detecting a concentration of the diatomic hydrogen in the gas of interest, and an analyzer for relating the spectral response of the gas of interest in combination with the detected concentration of the diatomic hydrogen to an energy content of the gas of interest, wherein the analyzer uses the detected concentration of diatomic hydrogen to compensate the energy content determined with respect to the spectral response of the gas of interest.

2. A system as claimed in claim 1, further comprising a pressure sensor for determining a pressure of the gas of interest, the analyzer further using the pressure to determine the energy content.

3. A system as claimed in claim 1, further comprising a temperature sensor for determining a temperature of the gas of interest, the analyzer further using the temperature to determine the energy content.

4. A system as claimed in claim 1, further comprising a pressure sensor for determining a pressure of the gas of interest and a temperature sensor for determining a temperature of the gas of interest, the analyzer further using the pressure and the temperature to determine the energy content.

5. A system as claimed in claim 1, further comprising an output optical fiber for transmitting the tunable signal to the gas cell.

6. A system as claimed in claim 1, further comprising an output optical fiber for transmitting the tunable signal to the gas cell, wherein the output optical fiber is single mode fiber.

7. A system as claimed in claim 1, further comprising an output optical fiber for transmitting the tunable signal to the gas cell, wherein the output optical fiber is polarization controlling fiber.

8. A method for monitoring a property of a gas of interest, comprising:
providing a sample of a gas;
generating a tunable signal with a semiconductor laser that is transmitted through the gas, wherein the step of generating the tunable signal comprises generating the tunable signal with a spectral width that is too broad to accurately detect a concentration of diatomic hydrogen due to associated narrow spectral lines of the diatomic hydrogen;
detecting the tunable signal after transmission through the gas to determine a spectral response of the gas;
detecting a concentration of the diatomic hydrogen in the gas of interest, and
relating the spectral response of the gas in combination with the detected concentration of the diatomic hydrogen to an energy content of the gas by using the detected concentration of diatomic hydrogen to compensate the energy content determined with respect to the spectral response of the gas.

9. A method as claimed in claim 8, further comprising:
determining a pressure of the gas; and
using the pressure to determine the energy content.

10. A method as claimed in claim 9, further comprising:
determining a temperature of the gas of interest; and
using the temperature to determine the energy content.

11. A system of gas property monitoring, comprising:
a gas cell for containing a gas of interest;
an external cavity semiconductor tunable laser spectroscopy system for generating a tunable signal that is transmitted through the gas of interest in the gas cell and detecting the tunable signal after transmission through the gas of interest to determine spectral response of gas of interest, the tunable laser comprising a semiconductor optical amplifier, a tunable filter, and a lens for coupling light between the semiconductor optical amplifier and the tunable filter;
an analyzer for relating the spectral response of the gas of interest to-an energy content of the gas; and
a hydrogen sensor for detecting a concentration of diatomic hydrogen in the gas of interest, and the analyzer relating a spectral response of the gas of interest and the detected concentration of the diatomic hydrogen of the energy content.

12. A system as claimed in claim 11, further comprising a pressure sensor for determining a pressure of the gas of interest, the analyzer further using the pressure to determine the energy content.

13. A system as claimed in claim 11, further comprising a temperature sensor for determining a temperature of the gas of interest, the analyzer further using the temperature to determine the energy content.

14. A system as claimed in claim 11, further comprising a pressure sensor for determining a pressure of the gas of interest and a temperature sensor for determining a temperature of the gas of interest, the analyzer further using the pressure and the temperature to determine the energy content.

15. A system as claimed in claim 11, further comprising an output optical fiber for transmitting the tunable signal to the gas cell.

16. A system as claimed in claim 11, further comprising an output optical fiber for transmitting the tunable signal to the gas cell, wherein the output optical fiber is single mode fiber.

17. A system as claimed in claim 11, further comprising an output optical fiber for transmitting the tunable signal to the gas cell, wherein the output optical fiber is polarization controlling fiber.

* * * * *